(12) United States Patent
Gupta et al.

(10) Patent No.: US 6,700,662 B2
(45) Date of Patent: Mar. 2, 2004

(54) PORTABLE LII BASED INSTRUMENT AND METHOD FOR PARTICULATE CHARACTERIZATION IN COMBUSTION EXHAUST

(75) Inventors: Sreenath B. Gupta, Naperville, IL (US); Ramanujam Raj Sekar, Naperville, IL (US)

(73) Assignee: The University of Chicago, Chicago, IL (US)

( * ) Notice: Subject to any disclaimer, the term of this patent is extended or adjusted under 35 U.S.C. 154(b) by 499 days.

(21) Appl. No.: 09/767,104

(22) Filed: Jan. 22, 2001

(65) Prior Publication Data

US 2002/0097397 A1 Jul. 25, 2002

(51) Int. Cl.[7] .......................... G01N 15/02; G01N 21/00
(52) U.S. Cl. .......................... 356/336; 356/338; 356/335
(58) Field of Search .............................. 356/337, 338, 356/335, 336, 334, 339, 392, 43, 46, 47, 315, 317, 318; 250/573–575, 554

(56) References Cited

U.S. PATENT DOCUMENTS 5,142,140 A * 8/1992 Yamazaki et al. ........ 250/222.2
6,154,277 A * 11/2000 Snelling et al. ............. 356/338
6,181,419 B1 * 1/2001 Snelling et al. ............. 356/335
6,473,178 B2 * 10/2002 Shimaoka ................... 356/336

OTHER PUBLICATIONS

Snelling et al. "Particulate Matter Measurements in a Diesel Engine Exhaust by Laser–Induced Incandescence and Standard Gravimetric Procedure" Oct. 1999, SAE Technical Paper Series 1999–01–3653, SAE International Fall Fuels and Lubricants Meeting.*

* cited by examiner

Primary Examiner—Russell Adams
Assistant Examiner—Andrew Sever
(74) Attorney, Agent, or Firm—Joan Pennington

(57) ABSTRACT

An improved instrument and method are provided for particulate characterization in combustion exhausts. An instrument for measuring particles of combustion exhausts includes a laser for producing a high intensity laser pulse. A sample cell receives a combustion exhaust input and the high intensity laser pulse. At least one detector detects a signal generated by particles in said received combustion exhaust input. The detected signal includes laser induced incandescence (LII). Signal conditioning electronics is coupled to the detector and particle data is displayed during transient operation of a combustion engine. Data related to mass concentration, number density, and particle size of particles in the received combustion exhaust input is measured and displayed.

19 Claims, 3 Drawing Sheets

PORTABLE LII BASED INSTRUMENT AND METHOD FOR PARTICULATE CHARACTERIZATION IN COMBUSTION EXHAUST

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to an instrument and method for particulate characterization in combustion exhausts, and more particularly relates to a method and portable instrument based on laser induced incandescence (LII) to measure particulate content and primarily mass emissions (gms/cm$^3$) of combustion exhausts, such as from diesel engines.

DESCRIPTION OF THE RELATED ART

Particles emitted from diesel engines pose a significant health hazard to the general public because these particles are of the right size to be inhaled and deposited deep inside the lungs. An additional concern is that certain substances that condense on the surface of these particles are carcinogenic.

Newer particulate standards imposed by the Environmental Protection Agency (EPA) have serious implications toward the future operation of combustion equipment. Current research efforts to curtail particulate emissions are limited by the lack of proper measurement techniques. The known measurement techniques require expensive instrumentation with equally matching demands on operator skill and time. One widely accepted EPA approved technique entails the collection of particulates using a filter paper in a diluted stream of exhaust gases, which is followed by gravimetry. Alternate measurement techniques are based upon light extinction or reflection principles. Efforts to obtain quantitative measurements based upon such principles have resulted in little success.

Techniques used in air sampling only are effectively used for measuring particle number concentrations, N (particles/cm$^3$). However, large response-times, such as 120 seconds, preclude their use for transient evaluations.

Laser induced incandescence (LII), a recently developed technique facilitates real-time quantitative planar imaging of soot emissions. A doctoral thesis by Sreenath B. Gupta at Pennsylvania State University in December, 1996 entitled "CHEMICAL MECHANISTIC APPROACHES TO SOOT CONTROL IN LAMINAR DIFFUSION FLAMES" describes the use of laser induced incandescence (LII) in characterizing the soot field in flames.

It is an object of the invention to provide an improved instrument and method for particulate characterization in combustion exhausts.

It is another object of the invention to provide an improved method and instrument based on laser induced incandescence (LII) to measure particulate content and primarily mass emissions (gms/cm$^3$) of combustion exhausts.

It is another object of the invention to provide an improved method and instrument based on laser induced incandescence (LII) to measure particulate content and primarily mass emissions (gms/cm$^3$) of combustion exhausts during transient operation of an engine.

It is another object of the invention to provide such improved method and instrument for measuring particle size in nanometers and number density or number of particles per cubic centimeter and mass concentration or grams of particles per cubic centimeter (gms/cm$^3$) of combustion exhausts during transient operation of an engine.

It is another object of the invention to provide such instrument that is a compact and portable device and that enables fast, easy, and cost-effective characterizing of particles of combustion exhausts.

It is another object of the invention to provide such improved method and instrument substantially without negative effect and that overcome many of the disadvantages of prior arrangements.

SUMMARY OF THE INVENTION

In brief, an improved instrument and method are provided for particulate characterization in combustion exhausts. An instrument for measuring particles of combustion exhausts includes a laser for producing a high intensity laser pulse. A sample cell receives a combustion exhaust input and the high intensity laser pulse. At least one detector detects a signal generated by particles in said received combustion exhaust input. The detected signal includes laser induced incandescence (LII).

In accordance with features of the invention, signal conditioning electronics is coupled to the detector and particle data is displayed during transient operation of a combustion engine. Data related to mass concentration, number density, and particle size of particles in the received combustion exhaust input is measured and displayed.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
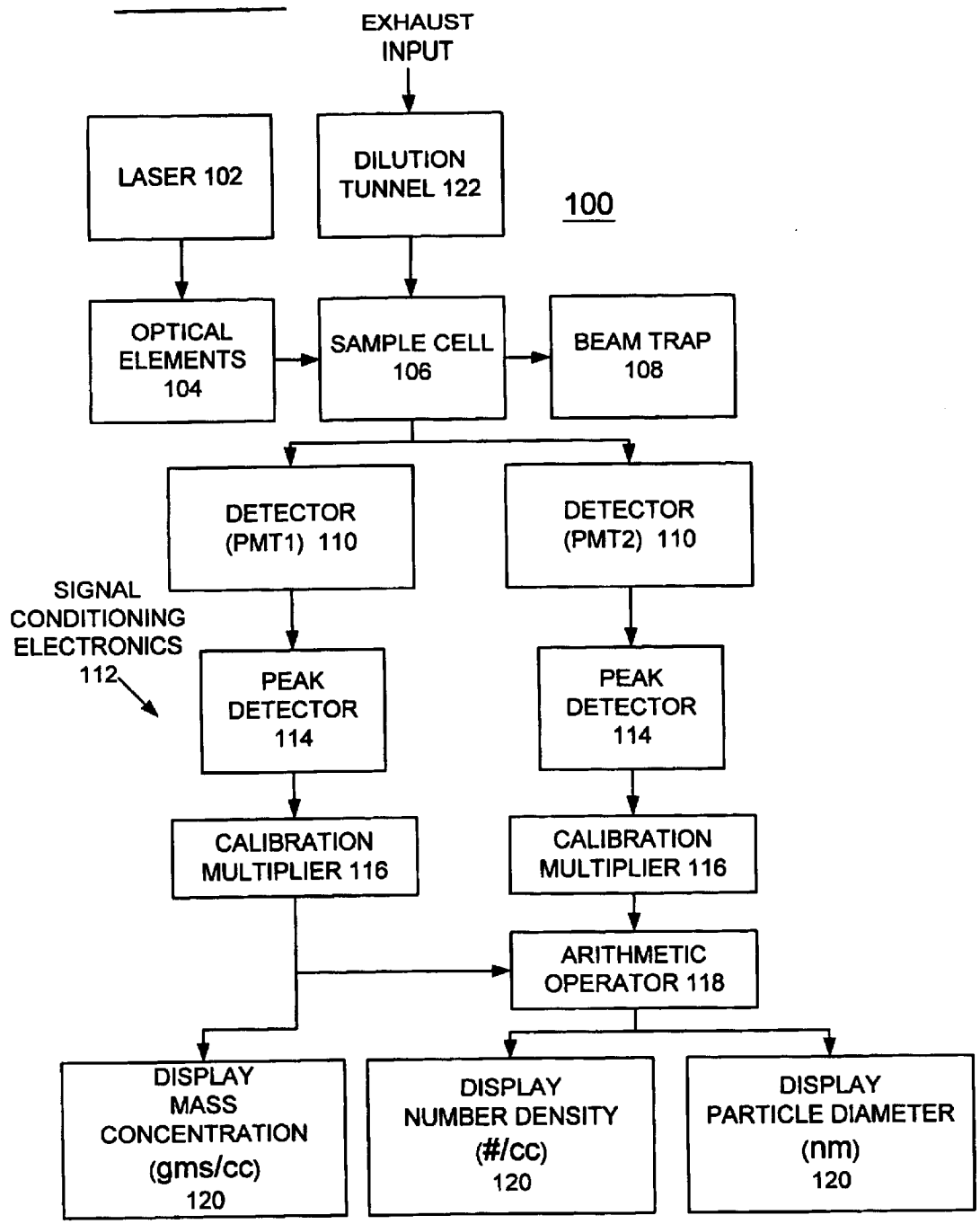
FIG. 1 is a block diagram representation of a portable instrument based on laser induced incandescence (LII) to measure particulate content and primarily mass emissions (gms/cm$^3$) of combustion exhausts, such as from diesel engines in accordance with the preferred embodiment.

Having reference now to the drawings, in FIG. 1 there is shown a block diagram representation of a portable instrument in accordance with the preferred embodiment based on laser induced incandescence (LII) to measure particulate content and primarily mass emissions (gms/cm$^3$) of combustion exhausts, such as from diesel engines, generally designated by the reference number 100. LII portable combustion exhaust measurement instrument 100 includes a laser 102 producing a high intensity laser beam pulse. The laser beam pulse is coupled through a plurality of optical elements 104 and applied to a sample cell 106. The sample cell 106 receives an exhaust input. Laser induced incandescence (LII) is used to measure particulate content and primarily mass emissions (gms/cm$^3$) of the combustion exhaust applied to the sample cell 106. A beam trap 108 is coupled to the sample cell 106.

In accordance with features of the preferred embodiment, with the laser induced incandescence (LII) technique, a high-energy laser pulse heats the tiny particles in combustion exhausts. Upon heating, the particles emit light, which, when collected appropriately, indicates particulate content and primarily mass emissions (gms/cm$^3$) of combustion exhausts. LII portable combustion exhaust measurement instrument 100 measures mean particle size in nanometers, number density or number of particles per cubic centimeter, and the mass concentration or grams per cubic centimeter. LII portable combustion exhaust measurement instrument 100 enables characterizing particles in a fast, easy, and cost-effective way. LII portable combustion exhaust measurement instrument 100 is used in real time, that is during transient operation of an engine. LII portable combustion exhaust measurement instrument 100 is a compact and portable instrument.

LII portable combustion exhaust measurement instrument 100 includes a plurality of detectors 110 coupled to the sample cell 106, such as a pair of photo-multiplier tube (PMT) detectors PMT1, PMT2 110. PMT detectors 110 detect a signal generated by particles in the combustion exhaust.

Signal conditioning electronics 112 is coupled to the detectors 110 to characterize, in real time during transient operation of an engine, particulate emissions in the combustion exhaust, such as of diesel engines. Signal conditioning electronics 112 includes a pair of peak detectors 114 respectively coupled to the PMT detectors 110 and providing a peak detected signal to a respective calibration multiplier 116. One of the calibration multipliers 116 provides a calibrated signal to a display 120 for displaying mass concentration (gms/cc) measured values in real time during transient operation of an engine. The calibration multipliers 116 are coupled by an arithmetic operator block 118 to display 120 for displaying number density (#/cc) and particle diameter (nm) measured values in real time during transient operation of an engine.

Figure 2:
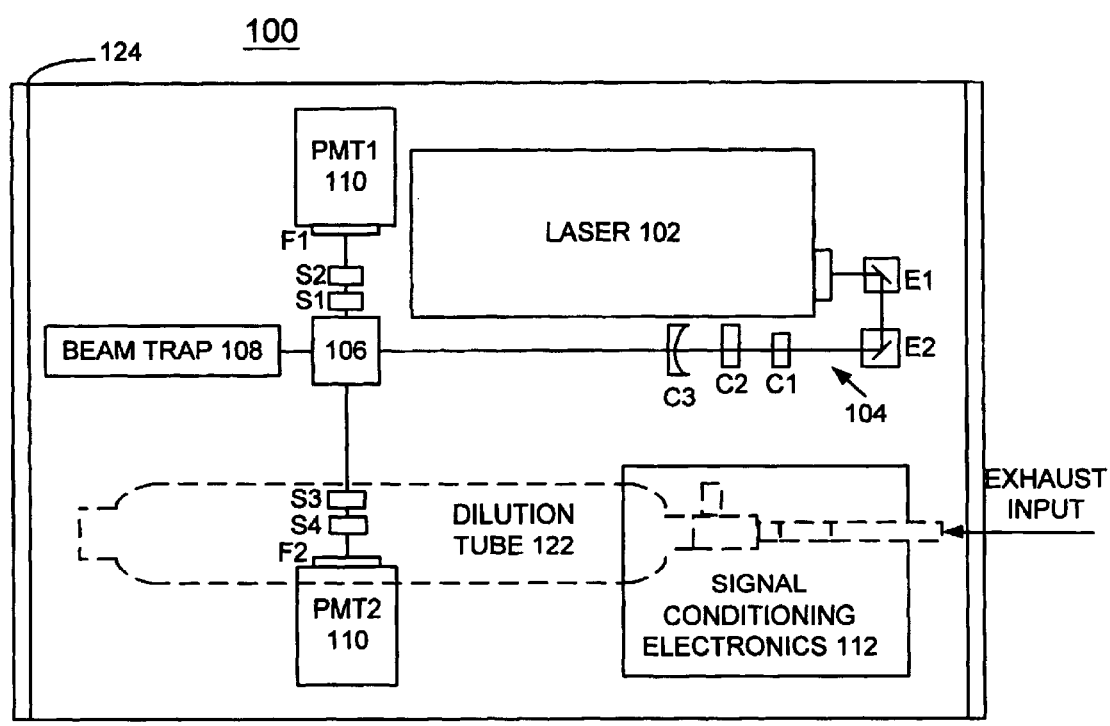
FIG. 2 is a diagrammatic top view of the portable instrument of FIG. 1 in accordance with the preferred embodiment.

In the LII portable combustion exhaust measurement instrument 100, the combustion exhaust stream is partially sampled by a vacuum generated by a dilution tunnel 122. In this tunnel 122 the exhaust sample stream is diluted using filtered air in a predetermined ratio. The diluted sample stream is then passed through the sample cell 106, to be finally exhausted out of the instrument 100. The high intensity emission from a pulsed laser 102 is expanded as a vertical sheet and focused onto the center of the sample cell 106 using multiple optical elements 104. The laser beam is finally terminated using the beam trap 108. Upon the incidence of the laser pulse, the particles in the combustion exhaust within sample cell 106 are heated to their sublimation temperature and emit thermal radiation as they cool down. This laser induced incandescence (LII) emission when appropriately collected by detectors 110 is directly proportional to the local mass concentration (gms/cc). This signal is focused using a train of optical elements including a first spherical lens S1, a second spherical lens S2 and an aperture with a blue interference filter F1 as shown in FIG. 2, onto a PMT1 detector 110. Similarly, the Rayleigh scattering signal is focused onto a second PMT2 detector 110. This signal is focused onto PMT2 detector 110 using a second set of optical elements including a first spherical lens S3, a second spherical lens S4 and an aperture with a green filter F2.

Signal conditioning electronics 112 is coupled to the PMT1, PMT2 detectors 110 reflect the following relations:

Mass concentration, $M$ (gms/cc) = calibration factor×signal from $PMT1$

Volumetric cross section, $Qvv$ = calibration factor×signal from $PMT2$

Mean particle size, $D$ (nm) = function1($M,Qvv$)

Number Density, $N$ (number of particles/cm3) = function2($M,Qvv$)

Respective signals from each PMT detectors PMT1, PMT2 110 are passed to a set of signal processing electronics 112. The peaks of the signals are detected by the peak detection circuitry 114, and then are further multiplied by calibration factors by the calibration multiplier circuitry 116. The resulting signals are further processed by an arithmetic operator 118 to obtain mean particle diameter (nm) and number density (number of particles/cm3). However, the processed signal from PMT1 110 directly results in mass concentration (gms/cc) and is routed to the numeric display 120.

In accordance with features of the preferred embodiment, LII portable combustion exhaust measurement instrument 100 provides data on the three parameters that are essential for understanding diesel exhausts; the mass concentration, number density, and mean size of the particles. LII portable combustion exhaust measurement instrument 100 by providing effective real time measurements can enable development of technologies to reduce particulate emissions. Certain transient phases of engine operation result in increased emission of particles, for example, an engine accelerating from idle. Because conventional instruments cannot measure particles during transient operation, engine designers are unable to fine-tune the engine parameters to reduce the emission of particles during transient operation. LII portable combustion exhaust measurement instrument 100 with its ability to collect information during transient operations can assist engine designers to design a cleaner-burning engine.

Figure 3:
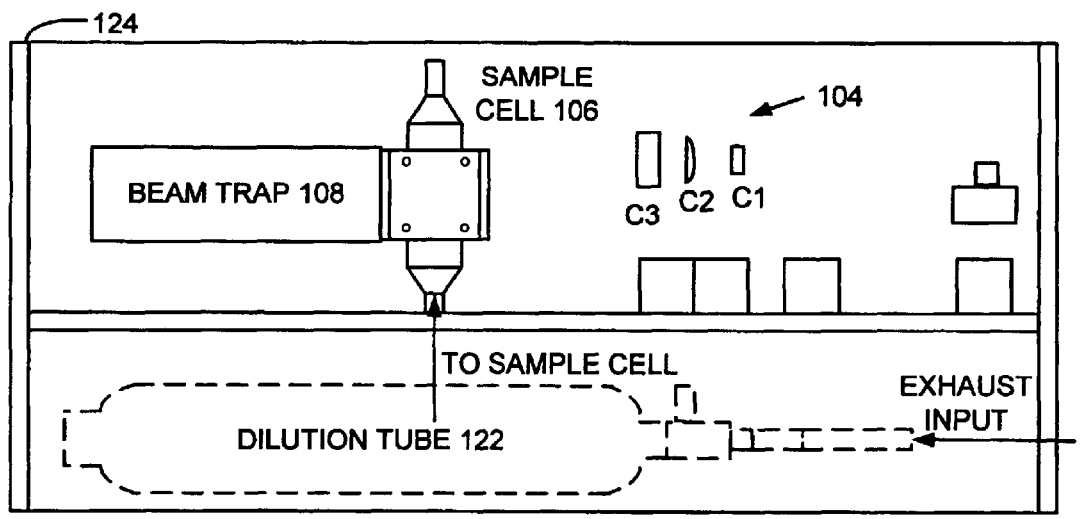
FIG. 3 is a diagrammatic front view of the portable instrument of FIG. 1 in accordance with the preferred embodiment.

Referring also to FIGS. 2 and 3, more details of optical elements 104 and signal focusing and filtering of the signal generated by the particles of the LII portable combustion exhaust measurement instrument 100 are shown. LII portable combustion exhaust measurement instrument 100 has a two layer construction. A top layer includes the laser 102, optical elements 104, the sample cell 106, detectors 110 and the signal conditioning electronics 112. A lower layer includes a dilution tunnel 122 shown in dotted line to dilute the exhaust sample using air. LII portable combustion exhaust measurement instrument 100 includes a housing 124 that contains the two layer construction. The display 120 is carried by the housing 124 for viewing measured results by the user.

As shown in FIG. 2, optical elements 104 includes a pair of elements E1, E1 for turning the laser beam through 90 degrees twice to pass through a plurality of cylindrical lenses C1, C2 and C3. The resulting laser beam passes through the sample cell 106. The beam trap 108 captures the laser beam from the sample cell 106. The signal generated by the particles is focused by two spherical lenses S1 and S2 onto the aperture/blue filter F1. This focused signal is filtered by a blue interference filter F1 before being detected by the PMTI detector 110. The Rayleigh scattering signal is similarly focused onto PMT2 detector 110 by two spherical lenses S3 and S4 onto the aperture/green filter F2.

While the present invention has been described with reference to the details of the embodiments of the invention shown in the drawing, these details are not intended to limit the scope of the invention as claimed in the appended claims.

What is claimed is:

1. An instrument for measuring particles of combustion exhausts comprising:
    a laser for producing a high intensity laser pulse;
    a sample cell for receiving combustion exhaust input and said high intensity laser pulse;
    a plurality of optical elements coupling said high intensity laser pulse to said sample cell; said plurality of optical elements including a plurality of cylindrical lenses; and
    at least one detector for detecting a signal generated by particles in said received combustion exhaust input, said signal including laser induced incandescence (LII).

2. An instrument for measuring particles of combustion exhausts as recited in claim 1 further includes a plurality of focusing elements coupling said signal generated by particles in said received combustion exhaust input in said sample cell to said at least one detector.

3. An instrument for measuring particles of combustion exhausts as recited in claim 1 includes a dilution tunnel coupling said combustion exhaust input to said sample cell.

4. An instrument for measuring particles of combustion exhausts comprising:
    a laser for producing a high intensity laser pulse;
    a sample cell for receiving combustion exhaust input and said high intensity laser pulse;
    at least one detector for detecting a signal generated by particles in said received combustion exhaust input, said signal including laser induced incandescence (LII); and
    a plurality of focusing elements coupling said signal generated by particles in said received combustion exhaust input in said sample cell to said at least one detector;
    said plurality of focusing elements including a plurality of spherical lenses.

5. An instrument for measuring particles of combustion exhausts as recited in claim 4 further includes a plurality of optical elements coupling said high intensity laser pulse to said sample cell.

6. An instrument for measuring particles of combustion exhausts as recited in claim 4 further includes a filter for filtering said signal generated by particles in said received combustion exhaust input.

7. An instrument for measuring particles of combustion exhausts as recited in claim 4 further includes signal conditioning electronics coupled to said at least one detector.

8. An instrument for measuring particles of combustion exhausts as recited in claim 7 wherein said signal conditioning electronics includes a peak detector.

9. An instrument for measuring particles of combustion exhausts as recited in claim 7 wherein said signal conditioning electronics includes a calibration multiplier.

10. An instrument for measuring particles of combustion exhausts as recited in claim 7 wherein said signal conditioning electronics includes a display for displaying particle measurements.

11. An instrument for measuring particles of combustion exhausts as recited in claim 4 includes a display coupled to said at least one detector for displaying data related to mass concentration, number density, and particle size of particles in said received combustion exhaust input.

12. An instrument for measuring particles of combustion exhausts as recited in claim 4 wherein said at least one detector for detecting a signal generated by particles in said received combustion exhaust input detects said signal during transient operation of an engine.

13. An instrument for measuring particles of combustion exhausts as recited in claim 4 wherein said at least one detector for detecting a signal generated by particles in said received combustion exhaust input includes at least one photo-multiplier tube (PMT) detector.

14. An instrument for measuring particles of combustion exhausts as recited in claim 4 wherein said at least one detector for detecting a signal generated by particles in said received combustion exhaust input includes a pair of photo-multiplier tube (PMT) detectors.

15. An instrument for measuring particles of combustion exhausts as receted in claim 14 includes signal conditioning electronics coupled to each of said pair of photo-multiplier tube (PMT) detectors.

16. A method for measuring particles of combustion exhausts comprising the steps of:
    utilizing a laser, producing a high intensity laser pulse;
    receiving a combustion exhaust input in a sample cell;
    coupling said high intensity laser pulse to said sample cell using a plurality of optical elements; said plurality of optical elements including a plurality of cylindrical lenses; and
    detecting a signal generated by particles in said received combustion exhaust input, said signal including laser induced incandescence (LII).

17. A method for measuring particles of combustion exhausts as recited in claim 16 further includes the steps of conditioning said detected signal and displaying data related to the particles in said received combustion exhaust input.

18. A method for measuring particles of combustion exhausts as recited in claim 17 wherein the step of displaying data related to the particles in said received combustion exhaust input includes the steps of displaying data related to mass concentration, number density, and particle size of particles in said received combustion exhaust input.

19. A method for measuring particles of combustion exhausts as recited in claim 16 wherein the step of detecting a signal generated by particles in said received combustion exhaust input includes the detecting a signal generated by particles in said received combustion exhaust input during transient operation of an engine.

* * * * *

(12) EX PARTE REEXAMINATION CERTIFICATE (6249th)
United States Patent
Gupta et al.

(10) Number: US 6,700,662 C1
(45) Certificate Issued: Jun. 10, 2008

(54) PORTABLE LII BASED INSTRUMENT AND METHOD FOR PARTICULATE CHARACTERIZATION IN COMBUSTION EXHAUST

(75) Inventors: Sreenath B. Gupta, Napervile, IL (US); Ramanujam Raj Sekar, Naperville, IL (US)

(73) Assignee: The United States of America as represented by the United States Department of Energy, Washington, DC (US)

Reexamination Request:
No. 90/007,500, Apr. 7, 2005

Reexamination Certificate for:
Patent No.: 6,700,662
Issued: Mar. 2, 2004
Appl. No.: 09/767,104
Filed: Jan. 22, 2001

(51) Int. Cl.
*G01N 21/71* (2006.01)

(52) U.S. Cl. .................. 356/336; 356/335; 356/338
(58) Field of Classification Search .................. None
See application file for complete search history.

(56) References Cited

U.S. PATENT DOCUMENTS

| | | | | |
|---|---|---|---|---|
| 4,254,336 | A | * 3/1981 | Rostler | 250/294 |
| 5,079,952 | A | * 1/1992 | Nakaso et al. | 73/624 |
| 5,142,140 | A | 8/1992 | Yamazaki et al. | 250/222.2 |
| 5,458,084 | A | * 10/1995 | Thorne et al. | 117/89 |
| 5,822,073 | A | * 10/1998 | Yee et al. | 356/445 |
| 5,982,478 | A | * 11/1999 | Ainsworth et al. | 356/28 |
| 5,991,048 | A | * 11/1999 | Karlson et al. | 356/445 |
| 6,104,536 | A | * 8/2000 | Eckhardt | 359/619 |
| 6,154,277 | A | * 11/2000 | Snelling et al. | 356/338 |
| 6,181,419 | B1 | 1/2001 | Snelling et al. | 356/335 |
| 6,473,178 | B2 | 10/2002 | Shimaoka | 356/336 |

OTHER PUBLICATIONS

Snelling et al., "Particulate Matter Measurements in a Diesel Engine Exhaust by Laser–Induced Incandescence and the Standard Gravimetric Procedure", 1999–01–3653, Oct. 1999, SAE (Society of Automotive Engineers), pp. 1–9.

Vander Wal et al, "Optical and Microscopy Investigations of Soot Structure Alterations by Laser–Induced Incandescence", Applied Physics B 67, Lasers and Optics, Feb. 16, 1998, pp. 115–123.

David R. Snelling et al., "Development and Application of Laser–Induced Incandescence (LII) as a Diagnostic for Soot Particulate Measurements", presented at: AGARD 90th Symposium of the Propulsion and Energetics Panel on Advanced Non–Intrusive Instrumentation for Propulsion Engines, Brussels, Belgium, Oct. 20–24, 1997, pp. 1–9.

Stefan Will et al., "Performance Characteristics of Soot Primary Particle Size Measurements by Time–Resolved Laser–Induced Incandescence", Applied Optics, vol. 37, No. 24, Aug. 20, 1998, pp. 5647–5658.

Gupta et al., "Real–Time Particulate Monitoring for Emissions Control", The DOE (United States Department of Energy) 1999 Annual Progress Report for Advanced Combustion and Emission Control, Oct. 1999, pp. 94–97.

\* cited by examiner

*Primary Examiner*—Erik Kielin

(57) ABSTRACT

An improved instrument and method are provided for particular characterization in combustion exhausts. An instrument for measuring particles of combustion exhausts includes a laser for producing a high intensity laser pulse. A sample cell receives a combustion exhaust input and the high intensity laser pulse. At least one detector detects a signal generated by particles in said received combustion exhaust input. The detected signal includes laser induced incandescence (LII). Signal conditioning electronics is coupled to the detector and particle data is displayed during transient operation of a combustion engine. Data related to mass concentration, number density, and particle size of particles in the received combustion exhaust input is measured and displayed.

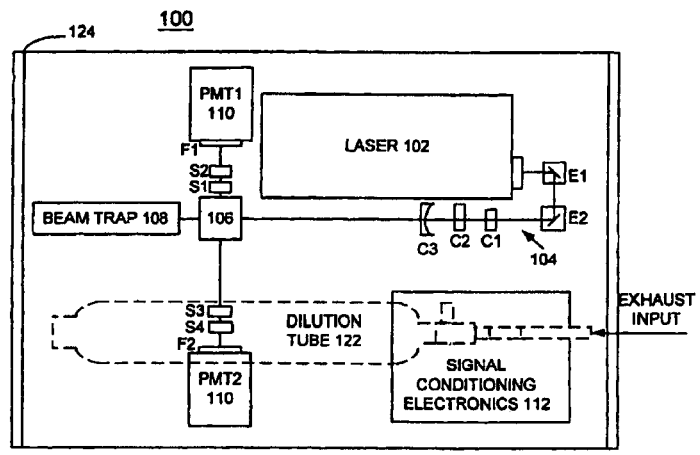

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–19 are cancelled.

* * * * *